United States Patent
Von Olleschikelbheim et al.

(10) Patent No.: US 9,261,502 B2
(45) Date of Patent: Feb. 16, 2016

(54) TEST SYSTEM FOR VISUAL ANALYSIS

(75) Inventors: Lars Von Olleschikelbheim, Münster (DE); Mark Hünken, Schwerin (DE); Marc Dangers, Schwerin (DE); Olaf Putensen, Schwerin (DE)

(73) Assignee: DST DIAGNOSTISCHE SYSTEME & TECHNOLOGIEN GMBH, Schwerin (DE)

( * ) Notice: Subject to any disclaimer, the term of this patent is extended or adjusted under 35 U.S.C. 154(b) by 8 days.

(21) Appl. No.: 13/390,834

(22) PCT Filed: Aug. 6, 2010

(86) PCT No.: PCT/EP2010/061525
§ 371 (c)(1), (2), (4) Date: Mar. 4, 2013

(87) PCT Pub. No.: WO2011/020724
PCT Pub. Date: Feb. 24, 2011

(65) Prior Publication Data
US 2013/0022965 A1  Jan. 24, 2013

(30) Foreign Application Priority Data

Aug. 17, 2009  (DE) .......................... 10 2009 037 791

(51) Int. Cl.
*G01N 33/543*  (2006.01)
*G01N 33/558*  (2006.01)

(52) U.S. Cl.
CPC ........ *G01N 33/558* (2013.01); *G01N 33/54386* (2013.01)

(58) Field of Classification Search
None
See application file for complete search history.

(56) References Cited

U.S. PATENT DOCUMENTS

| | | | |
|---|---|---|---|
| 4,943,522 A | 7/1990 | Eisinger et al. | |
| 6,316,205 B1 * | 11/2001 | Guan et al. | 435/7.1 |
| 6,916,666 B1 * | 7/2005 | Mendel-Hartvig et al. | 436/518 |
| 7,405,084 B1 * | 7/2008 | Mendel-Hartvig et al. | 436/518 |
| 2003/0119203 A1 * | 6/2003 | Wei et al. | 436/514 |
| 2008/0057595 A1 | 3/2008 | Schwertner et al. | |
| 2009/0221101 A1 * | 9/2009 | Jerome et al. | 436/518 |

FOREIGN PATENT DOCUMENTS

| | | |
|---|---|---|
| EP | 0063810 A1 | 11/1982 |
| EP | 0119613 A2 | 9/1984 |
| EP | 0171150 A2 | 2/1986 |
| EP | 1718970 A2 | 11/2006 |
| WO | WO-8401031 A1 | 3/1984 |
| WO | WO-02088739 A1 | 11/2002 |
| WO | WO-2007063423 A1 | 6/2007 |
| WO | WO 2007/122403 A1 * | 11/2007 |
| WO | WO-2007122403 A1 | 11/2007 |

* cited by examiner

*Primary Examiner* — Chris L Chin
(74) *Attorney, Agent, or Firm* — Drinker Biddle & Reath LLP

(57) ABSTRACT

The present invention relates to a test system for visual analysis and to the use thereof in the point-of-care testing field.

13 Claims, 2 Drawing Sheets

Preferred embodiment: 2 reference fields (top and bottom), main field (middle)

TEST SYSTEM FOR VISUAL ANALYSIS

CROSS-REFERENCE TO RELATED APPLICATIONS

This application is a national stage application (under 35 U.S.C. §371) of PCT/EP2010/061525, filed Aug. 6, 2010, which claims benefit of German application 10 2009 037 791.3, filed Aug. 17, 2009.

The present invention relates to a test system for visual analysis and the use of the same in the point-of care testing field.

In research, diagnostics or a multiplicity of further fields of use, analytic laboratory tests serving for qualitative or/and quantitative determination of molecules, analytes or the activity or composition thereof represent the basis for far-reaching statements up to the development of new methods or devices. The basis is the generally known methods of DNA/RNA analytics or protein analytics. Another example is the multiplicity of analytic processes and methods which are used for determining (bio) markers and many other substances/analytes.

Fast test methods are known such as the lateral flow test (LFT), flow-through test (FTT), agglutination test (AT) or the solid-phase test (SPT). All these methods serve for a fast detection of analytes without using apparatuses and are suitable for visual analysis.

A robust assay principle is known, as described in the prior art with respect to in vitro diagnostics as immunoassay (IA), in particular as EIA or "binding assay" (sandwich") (see e.g. EP 0 171 150 B1, EP 0 063 810 B1). Furthermore, e.g., the fluorometric detection of IgE within a binding assay is known from EP 0 119 613 B1. Moreover, reference is made to the literature of Roger P. Ekins (e.g. WO 8401031 and others).

Furthermore, a membrane-based binding assay, in particular of IgE from blood, on allergens is known since end of the 1980s. E.g. CHEMICAL ABSTRACTS, vol. 101, no. 25, 17, Dec. 1984, page 578, abstract no. 228190b, Columbus, Ohio, US; B. J. WALSH et al.: "Allergen discs prepared from nitrocellulose: detection of IgE binding to soluble and insoluble allergens", & J. IMMUNOL. METHODS 1984, 73(1), 139-45.

For the point-of-care (POC) testing field, for example, the commercially available fast check POC of the applicant is described (see EP 1 718970), which can be used on the basis of a membrane-supported binding assay for allergy detection from whole blood.

However, there is a high demand to improve the significance of a visually readable test system.

A particular problem is the difficulty to reliably evaluate with the naked eye and without technical aids an intensity contrast with more greyscales than "bright" and "dark". In a point-of-care test, this is absolutely necessary because a rapidly evaluable result without additional aids (e.g. reader, visual aids etc) has to be ensured.

A plurality of test systems which are based on the principle of the lateral flow assay (e.g. Phadia Rapid (www.phadia.com)) is commercially available. In this test, the antibodies in the blood against specific antigens are detected in that an antigen on a detection strip is fixed on a carrier membrane, the antibodies from the sample adhere on this antigen, and a marked antibody binds on said antibody from the sample. Marking, in this case with gold nanoparticles, makes the strip appear colored as soon as enough marked antibodies have bound. In proximity to the detection strip, there is a control strip on which a mixture of different human IgE is fixed. The marked antibody thus binds at the control field, but independent of the presence of specific IgE in the sample and therefore always, provided that the membrane strip and the marked antibody are fully functional.

The fast POC check test of the applicant (supra, EP 1 718 970) is based on a fixed antigen to which antibodies from a sample bind. After a washing step, an antibody marked with the enzyme alkaline phosphatase is added, which antibody binds to the first antibody. After a further washing step, a substrate for the enzyme is added which darkens during its conversion so that a dark strip occurs on the detection place. This detection reaction is stopped with a stop solution to prevent that the low number of nonspecifically bound marked antibodies alone already causes a darkening.

Further examples are the CLA system of Hitachi, and the allergen disk system of Dr. Fooke. All examples are based on a visual detection of a color-changing or darkening strip or otherwise formed sample carriers.

However, none of the methods allows quantification beyond the two values "bright" and "dark" since the human eye is not capable to objectively determine absolute brightness values.

In contrast, the test "Combur" marketed by Hoffmann-LaRoche (CH) and similar urine strip tests differ from the aforementioned tests because they comprise a multiplicity of test fields. They are based on different assay principles; however, what all have in common is a change in color intensity from colorless/white to color-intense which can be visually evaluated. For this purpose, colored areas are printed on the packaging of the Combur test by means of which the user can assess and classify the extent of the discoloration from the test.

However, a disadvantage of this method is that a printed reference field does not provide information or control with respect to a correct procedure of the test. If desired, this information has to be provided through additional control fields, whereby the capacity of the test strip with regard to the number of readable tests is reduced.

It is therefore an object of the present invention to provide an improved visual analysis for a test system.

The object is achieved in that the test system generates different brightness levels for the visual viewer which enables an advantageous safe analysis.

DETAILED DESCRIPTION

Figure 1:
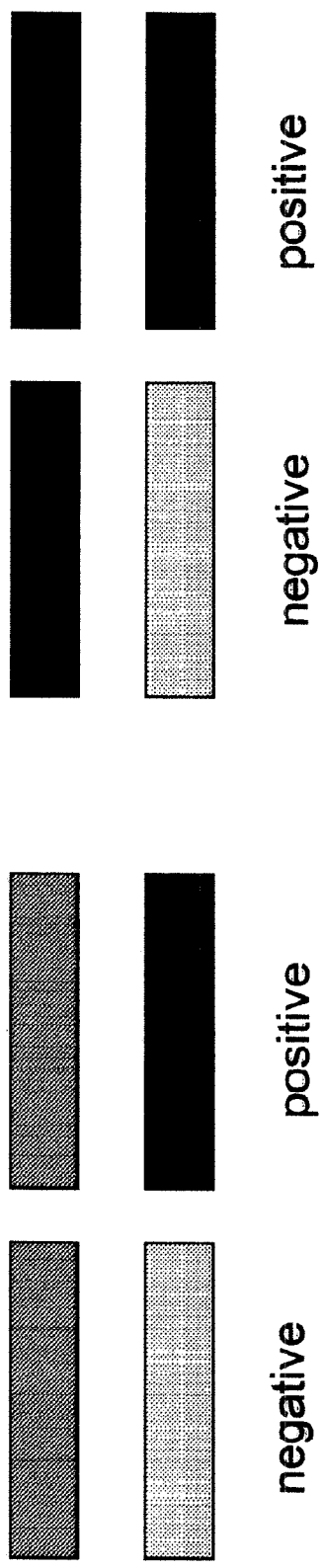
FIGS. 1 and 2 illustrate an arrangement of bars which, in addition, are optically distinguishable from each other because said bars have spaces (recesses) therebetween.
Figure 2:
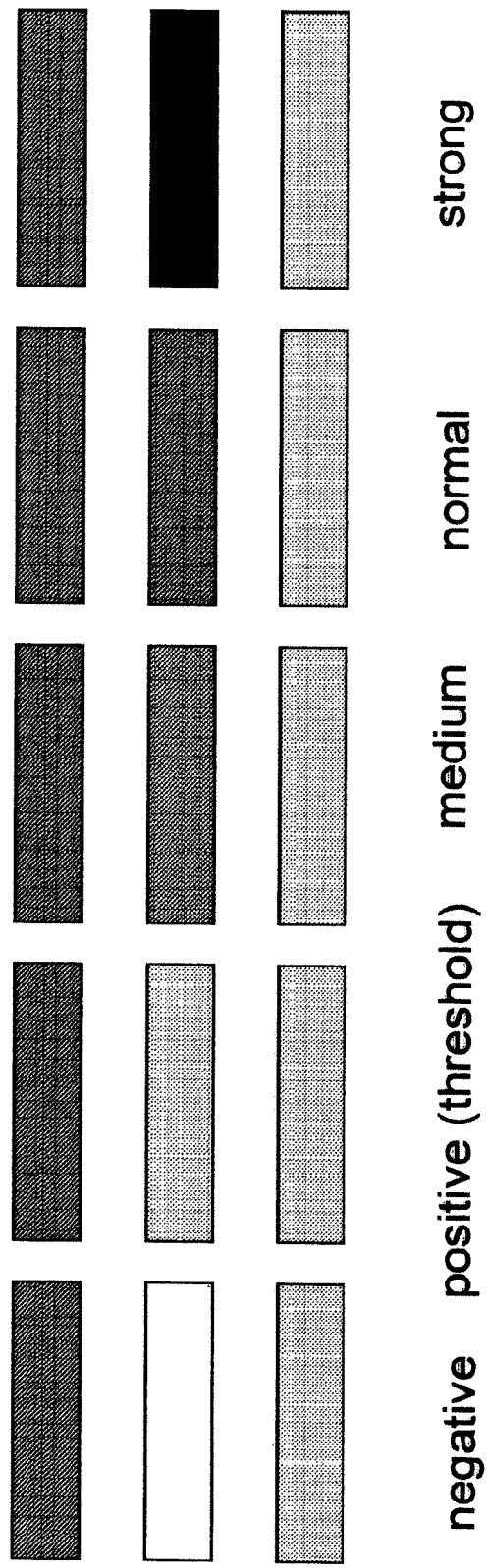

Therefore, the invention relates to a test system for visual analysis, preferably for the naked eye and without further aids, which comprises an analysis unit.

This analysis unit of a test system for visual analysis of a test result consists of at least two optically distinguishable fields,
wherein at least one (main) field has receptor molecules of a species,
and at least one further (reference) field has a lower density of receptor molecules of a species,
wherein all receptor molecules of a species are fixed on a carrier,
wherein the fields for a fluid sample containing one or a plurality of binders are wettable and the binding success is detected with a detection agent so that the analysis unit generates different brightness levels (e.g. greyscales).

For producing fields with low density, the receptor molecules can account for 10 to 90% by weight, in particular 20 to 80% by weight relative to the main field which comprises 100% by weight of receptor molecules.

This analysis unit allows a safe visual analysis with the naked eye and utilizes the fact that the eye cannot determine absolute brightness, but can identify relative brightness differences.

Particularly advantageous, the analysis unit according to the invention allows to detect relative threshold values for the respective binder/analyte on a receptor molecule in an analysis unit.

In a further embodiment, the optically distinguishable fields on an analysis unit are spatially separated from each other. This can be achieved, e.g., with recesses on the carrier or can be implemented in any other manner.

Furthermore, it is preferred that one or a plurality of main fields is surrounded in an analysis unit by at least two (reference) fields with a lower density of receptor molecules. The reference fields, amongst each other, preferably have in each case a different density. For example, in two reference fields, in each case a density of 10 and 90%, 20 and 80% or 30 and 70% is set.

In a further embodiment, the reference field can have different or the same species of receptor molecules as the main field. However, important is that at least one binder in the main field and/or reference field binds to a receptor molecule in an analysis unit.

If, e.g., the brightness in the main field remains unchanged and the brightness in the reference field is changed, the test is negative.

In the case of an allergy test or food incompatibility test, the receptor molecule can be an antigen, whereas the reference fields, e.g., have receptor molecules of a species which molecules can be obtained from another source, in particular from blood plasma, or can be produced synthetically. In particular, this can involve antibodies, and in particular immunoglobulins such as IgE, IgA1, IgA2, IgA3, IgA4, IgG or IgG1-4.

Based on this, a receptor molecule in a reference field can be identical to a binder which binds in the main field to the receptor molecules.

Therefore, in a further embodiment, the invention relates to such an embodiment, wherein at least one reference field has a receptor molecule of a species which is identical to a binder for a receptor molecule in the main field.

It is further preferred in this embodiment that a detection agent binds to the binder of the reference field and binds the identical binder of the main field, which binder is present in the case of a positive result, and causes the change in brightness or color. In particular, the detection agent can be a secondary antibody against the primary antibody (=binder), in particular against immunoglobulins such as IgE, IgA1, IgA2, IgA3, IgA4, IgG or IgG1-4. The secondary antibody (=detection agent) is preferably marked with gold nanoparticles, quantum dots or fluorescent particles, amongst which in particular fluorescence dyes are preferred, or with enzymes such as the alkaline phosphatase which reacts with a substrate and causes a change in brightness or in color in this manner. In a further embodiment, the analysis unit includes a control field, wherein independent of the sample fluid, brightness is obtained. Here, brightness is achieved through the detection agent. This, e.g., can be a field, wherein the receptor molecule is saturated with a binder. Thus, such a control field can be a positive or negative control.

Another preferred embodiment relates to an arrangement wherein the main field is surrounded by a control field and a field of lower density.

Such an embodiment, for example, is an arrangement of bars which, in addition, are optically distinguishable from each other because said bars have spaces (recesses) therebetween (see figures).

In a particularly preferred embodiment, a plurality of analysis units according to the invention with identical, but preferably different receptor molecules of a species are applied on a carrier thereby forming a test system, preferably arranged in the form of a coordinate system.

This advantageously allows the simultaneous determination of a plurality of receptor molecules, in particular more than 5 and in particular more than 8 receptor molecules, of different species in independent analysis units with a sample fluid.

Preferably, the test system or the respective analysis unit is used for the diagnosis of diseases and food incompatibility in animals and humans. For example, this is preferred for determining allergies, wherein allergens represent such receptor molecules, and the binder, such as immunoglobulins, can be detected directly from the blood.

Other diseases are diseases such as cardiovascular diseases, diabetes, etc.

In a further preferred embodiment, the test system is suitable for the point-of-care testing field. For this, the test system has to be present in a chamber. It is further preferred that the dimensions are pocket-sized and the test system has a length of up to 20 cm, a height of up to 10 cm and a width of up to 20 cm. These sizes allow a manageable and mobile handling so that in the point-of-care testing field, a fast analysis can be performed.

Within the context of this invention, point-of-care is to be understood as:

Carrying out laboratory tests in immediate proximity to the patient, outside of a central laboratory;

No sample preparation, in particular no pipetting, the test material is preferably whole blood;

Ready-to-use reagents, for example in the form of tanks or cassettes;

Measuring devices which are provided only for individual sample measurements;

No extensive medical-technical education is necessary for the use;

Therefore, the invention also relates to the use of the test system according to the invention in the point-of-care testing field.

Furthermore, the invention relates to a corresponding method for diagnosing diseases, in particular allergies and food incompatibility, wherein a sample fluid is applied on at least two optically distinguishable fields of a readout unit, wherein at least one field has receptor molecules of a species, and at least one further field has a lower density of receptor molecules of a species, wherein all receptor molecules of a species are fixed on a carrier, wherein the fields are wetted with the sample fluid containing one or a plurality of binders and the binding success is detected with a detection agent so that the analysis unit generates different brightness levels (e.g. greyscales).

Further configurations according to the method derive from the aforementioned embodiments.

The terms "with the naked eye" or "visually" are used synonymously and mean in each case that the change in brightness caused during the detection can be identified by the human eye without further technical aids, in particular without the need of a readout device.

The term "field" is used as a synonym for "detection place".

The readout value of the test method according to the invention can be the brightness of a point or an area which changes during the detection by means of the detection agent in such a manner that it can be visually identified. In presence of the analyte, the brightness can be increased or decreased. "Brightness" can also be understood as a change in color. "Darkness" is likewise the result of a change in brightness.

Further examples for "brightness" comprise also color saturation of a colored test reagent, a change in color of a test reagent, the change in size or of other flat structural elements of a point or a surface, the change of other optical material properties such as gloss, transparency, granularity of a surface. Combinations of these changes can be preferred. Therefore, changes in brightness from "white" to "grey" to "black" or vice versa can take place. Preferably, for establishing a contrast, the visible carrier is coated "white" or "black" or in any other suitable manner.

The intensity of a readout value is its visually detectable property or properties which change during the detection process.

The binder is preferably an analyte and can be any substance or substance mixture, optionally including a solvent, of any origin, in particular from a plant or an animal, preferably a mammal, and particularly preferred from a human. According to the invention, the binder or analyte is integral part of a sample fluid, cleaned or pure, which, however, comes from a body fluid and can be pretreated. Preferred are body fluids such as whole blood, half blood, EDTA stabilized blood, serum, saliva, lacrimal fluid, urine or brain fluid. In the broadest sense, the binder is addressed to the receptor molecules.

The fields according to the invention are located on a (detection) carrier in such a spatial proximity that both fields, when visually looking at them, lie in the same field of view. Preferred is a (detection) carrier that has more than one field. Preferred are (detection) carriers to which further test reagents which are helpful for the detection can be fed, for example with a pipette or pump or through capillary force. Particularly preferred are detection carriers onto which fluids are fed in micro channels, wherein the carrier is set up in a chamber.

The fields can be located directly on the substrate of the detection carrier or on a coating. Preferred are gels or membranes, in particular nitrocellulose membranes, on or in which the receptor molecules or test reagents are located. Preferably, at least one receptor molecule or test reagent is fixed, for example immobilized, spotted or the like, on or in the membrane. It can be preferred that more than one membrane is located on the detection carrier, in particular that each analysis unit is located on its own membrane, or a detection place and at least one associated comparison place, or a plurality of detection and comparison places are located on a membrane. Furthermore, it can be preferred to position a plurality of analysis units on a membrane, and separated therefrom, a plurality of analysis units on another membrane.

The intensity of the readout values changes during detection on the detection place as well as on the associated comparison places in the same direction.

It can be preferred that the detection carrier according to the invention contains structures which make visual determination easier; these are in particular optical elements such as, for example, transparent or milky windows, lenses, Fresnel lenses, beam splitters, lattices, holograms or other digital optical elements which allow directly viewing the places. The execution according to the invention of the detection also includes artificial lighting which is perceived by the user as being advantageous, and lighting which can be selective in a certain spectral range. This spectral range can comprise the IR or the UV range which are not directly visually perceptible on the excitation side, but generate a readout value in the visible range during the detection process.

According to the invention, the area of the fields is large enough to enable visual determination directly or by means of the integrated optical elements. The fields can be formed round, elliptical, oval, triangular, polygonal, square or rectangular, in particular in the form of a strip or bar, or entirely irregular. It can be divided, for example in two strips, or ring-shaped with an unchangeable region inside the place.

It can be advantageous to structure a strip with visible elements, in particular with strips which are arranged transverse to a strip-shaped detection place and, in the case of a positive detection, are visible as "+", and in the case of a negative detection, are visible as "−". Furthermore, it can be preferred to provide the fields with a readable designation, for example the name of an allergen, or with an abbreviated designation, or with a barcode, matrix code, dot code or other machine-readable designations.

It can further be preferred to apply or print onto the carrier at least one readout value as additional visual control, in particular grey or color values which are not subject to a detection or control reaction and therefore allow to additionally compare a reference place or detection place with reference values which provide comparison values with respect to the readout values independent of any detection reaction.

The reference field is set, for example, through the predefined concentration or amount of a receptor molecule or test reagent, in particular of an antigen or antibody, in such a manner that its brightness is neither 100% of the possible change in brightness or color at the detection place, nor 0%. Preferred are values between 30% and 70%, in each case on a linear or logarithmic scale. It can be preferred to set a comparison place with a value of 50%.

At said reference fields, the invention delivers readout values which, like the readout values at the fields, depending on the detection process, show a more or less significant change with respect to the initial value. This concordant variation of the readout value is of advantage because in this manner, the detection becomes tolerant with respect to changes in the detection process. For example, in the case of incubation times which are extended or shortened with respect to the specified detection process, the possibility to compare between detection place (the main field) and reference field is maintained.

Another advantage is that batch-to-batch variations of some detection reagents can be identified. For example, in the case of an antibody which is conjugated with alkaline phosphatases, a variation of its apparent binding constant, apparent enzyme turnover or of the quality of the enzyme substrate can occur. In all these cases, the readout values for detection places and comparison places vary concordantly and, despite the variation, allow visual determination.

In a preferred embodiment, at least two reference fields are in the same field of view as the detection place (above, main field). Here, the detection in at least two reference fields is set differently so that the changes in brightness or color of the control places can be visually distinguished, wherein the naked eye can determine the change in brightness or color at the detection place as stronger than the stronger control field, equally strong as the strong control field, between strong and weaker control field, equally weak as the weaker control field, or weaker than the weakest control field, up to "not existent".

Preferred is an arrangement in which the detection place (main field) lies between two associated control places.

The control places, for example, are set through predefined concentrations or amounts of a test reagent, in particular an antibody, in such a manner that their brightness in each case is neither 100% of the possible change in brightness or color at the detection place, nor 0%. Particularly preferred in the case of two control places are values in pairs of 20% and 80%, particularly preferred of approximately 30% and 70% on a linear or logarithmic scale.

In a preferred embodiment, a binding assay is used for the detection between receptor molecules and binders such as peptides and/or proteins, in particular a binding between antibody and antigen, antibody and antibody, receptor and ligand, or DNA, RNA, PNA, LNA and DNA, RNA, PNA, LNA. The invention includes the detection when different molecules bind to each other, for example aptamers to proteins or PNA to RNA. It can be advantageous to set up the detection from a plurality of binding reactions, for example by using primary and secondary antibodies.

Detection means are all detection means and their methods for binding reactions.

In a preferred embodiment, at least one of the test reagents is marked such that in the case of a positive detection, it can be visually identified on the field and on the reference field. Particularly preferred is the marking with gold nanoparticles, quantum dots or fluorescent particles, amongst which in particular fluorescence dyes are preferred.

In a further preferred embodiment, at least one of the test reagents is marked with an enzyme, and at least one further test reagent is a substrate that is converted by the enzyme and thereby causes at least on the comparison place and in the case of a positive detection also on the detection place, a change in intensity of the readout value which is visible with the naked eye. Particularly preferred is this embodiment of a detection system if it is structured analog to an Elisa detection system. In this case, a molecule, for example an antigen or a food incompatibility antigen, is fixed on the detection carrier to which an antibody from the sample binds. To this sample antibody binds an antibody from the test reagent which is marked with an enzyme, for example alkaline phosphatase. In a further step, a substrate is fed which is converted by the enzyme and thereby causes a change in the intensity of the readout value. It can be preferred to provide the substrate with a marking, for example with a fluorescence dye, which, due to the changed interaction when eliminating a portion of the substrate, fluoresces more intensely or less intensely, or with two fluorescence dyes which mutually quench each other and during the dissociation of the substrate are separated and fluoresce more intensely, or with two fluorescence dyes between which an energy transfer takes place and which, during the dissociation of the substrate, are present with a seemingly smaller Stokes shift.

In a preferred embodiment, at least one antigen is fixed on the field, to which antigen, an antibody from the sample binds to which antibody, in turn, a marked antibody binds, and antibodies which do not come from the sample are fixed on a comparison place, wherein the marked antibody binds to said antibodies.

The invention claimed is:

1. An analysis unit of a test system for visual analysis of a test result, consisting of at least two optically distinguishable fields,
    wherein at least one first field has receptor molecules of a species, wherein the receptor molecules of a species are at least one allergen,
    and at least one further field has a lower density of receptor molecules of a species, wherein all receptor molecules of a species are fixed on a carrier,
    wherein the fields are wettable for a fluid sample containing one or a plurality of binders, wherein the binder is at least one immunoglobulin, and the binding success is detected with a detection agent so that the analysis unit generates different brightness levels, and
    wherein the test system is an allergy test or a food incompatibility test,
    and wherein optionally, a further field has an immunoglobulin.

2. The analysis unit for a test system for visual analysis of a test result according to claim 1, wherein fields with a lower density have receptor molecules with 10 to 90% by weight of receptor molecules relative to the first field.

3. The analysis unit for a test system for visual analysis of a test result according to claim 1, wherein the receptor molecules in the fields are the same or different.

4. The analysis unit for a test system for visual analysis of a test result according to claim 1, wherein at least a reference field has a receptor molecule of a species which is identical to a binder for a receptor molecule in the first field.

5. The analysis unit for a test system for visual analysis of a test result according to claim 1, wherein the optically distinguishable fields are spatially separated from each other and, in particular, the fields can be formed round, elliptical, oval, triangular, polygonal, square or rectangular, in particular in the form of an elongated strip or bar.

6. The analysis unit for a test system for visual analysis of a test result according to claim 1, wherein the test system is a disease test.

7. The analysis unit for a test system for visual analysis of a test result according to claim 1, wherein the sample fluid is a body fluid.

8. The analysis unit for a test system for visual analysis of a test result according to claim 7, wherein the body fluid is whole blood, half blood, EDTA stabilized blood, serum, saliva, lacrimal fluid, urine or brain fluid.

9. A test system containing one or a plurality of analysis units according to claim 1, wherein the test system is in the form of a coordinate system.

10. A point-of-care testing field which comprises the analysis unit according to claim 1.

11. An analysis unit of a test system for visual analysis of a test result, consisting of at least two optically distinguishable fields,
    wherein at least one first field has receptor molecules of a species, wherein the receptor molecules of a species are at least one allergen,
    wherein each further field has a different density of receptor molecules, and at least one further field has a lower density of receptor molecules of a species,
    wherein all receptor molecules of a species are fixed on a carrier,
    wherein the fields are wettable for a fluid sample containing one or a plurality of binders, wherein the binder is at least one immunoglobulin, and the binding success is detected with a detection agent so that the analysis unit generates different brightness levels, and
    wherein the test system is an allergy test or a food incompatibility test and wherein optionally, a further field has an immunoglobulin.

12. A method for diagnosing an allergy or a food incompatibility comprising
    applying a sample fluid onto at least two optically distinguishable fields of a readout unit, wherein at least one field has receptor molecules of a species of an antigen indicative of the allergy or the food incompatibility and at least one further field has a lower density of receptor molecules of the species, wherein all receptor molecules of a species are fixed on a carrier, wherein the fields are wetted with the sample fluid containing one or a plurality of binders, wherein the binder is at least one immunoglobulin, detecting the binding success with a detection agent that generates different brightness levels in an analysis unit, and comparing with the naked eye the brightness levels of the least one field and the at least one further field, wherein the allergy or the food incompatibility is diagnosed when the brightness level of the at least one field changes relative to the brightness level of the at least one further field.

13. The analysis unit for a test system for visual analysis of a test result according to claim 1, wherein fields with a lower density have receptor molecules with 20 to 80% by weight of receptor molecules relative to the first field.

* * * * *